United States Patent
Mensa et al.

(10) Patent No.: US 10,256,084 B2
(45) Date of Patent: Apr. 9, 2019

(54) PORTABLE ELECTRONIC DEVICE FOR THE ANALYSIS OF A GASEOUS COMPOSITION

(71) Applicant: NANOTECH ANALYSIS S.R.L.S., Turin (IT)

(72) Inventors: Gianpiero Mensa, Turin (IT); Raffaele Correale, Turin (IT)

(73) Assignee: NANOTECH ANALYSIS S.R.L., Turin (IT)

( * ) Notice: Subject to any disclaimer, the term of this patent is extended or adjusted under 35 U.S.C. 154(b) by 112 days.

(21) Appl. No.: 15/323,279

(22) PCT Filed: Jul. 2, 2015

(86) PCT No.: PCT/IB2015/054992
§ 371 (c)(1),
(2) Date: Dec. 30, 2016

(87) PCT Pub. No.: WO2016/005864
PCT Pub. Date: Jan. 14, 2016

(65) Prior Publication Data
US 2017/0133212 A1    May 11, 2017

(30) Foreign Application Priority Data
Jul. 7, 2014    (IT) .............................. MI2014A1228

(51) Int. Cl.
*H01J 49/04* (2006.01)
*H01J 49/00* (2006.01)
(Continued)

(52) U.S. Cl.
CPC ...... *H01J 49/0422* (2013.01); *G01N 33/0016* (2013.01); *H01J 49/0022* (2013.01);
(Continued)

(58) Field of Classification Search
USPC ......................................... 250/288, 281, 282
See application file for complete search history.

(56) References Cited

U.S. PATENT DOCUMENTS

| 5,481,110 A | 1/1996 | Krishnaswamy et al. |
| 7,767,959 B1 | 8/2010 | Friedhoff et al. |

(Continued)

FOREIGN PATENT DOCUMENTS

| EP | 2273531 A1 | 1/2011 |
| WO | 2014/105089 A1 | 7/2014 |

OTHER PUBLICATIONS

International Search Report for PCT/IB2015/054992, dated Oct. 23, 2015.

*Primary Examiner* — Kiet T Nguyen
(74) *Attorney, Agent, or Firm* — Arent Fox LLP; Michael Fainberg

(57) ABSTRACT

An electronic device 1 for analyzing a gas composition, which is present in an environment A at an environment pressure Pa, is described. The device 1 is portable and comprises a gas sampling module 7, an ion filtering module 8 and an ion detecting module 9. The sampling module 7 is configured to adjust an input gaseous flow Fi of gaseous particles from the environment A and to ionize said gaseous particles and to generate an ion flow I having an ion composition representative of the gas composition to be analyzed. The ion filtering module 8 is configured to controllably select at least one type of ions present in the ion flow I and to generate a corresponding at least one homogeneous ion beam I'. The ion detecting module 9 is configured to measure the intensity of such least one ion beam I'.

15 Claims, 13 Drawing Sheets

(51) Int. Cl.
    *G01N 33/00*         (2006.01)
    *H01J 49/14*         (2006.01)
    *H01J 49/24*         (2006.01)

(52) U.S. Cl.
    CPC ........ *H01J 49/0427* (2013.01); *H01J 49/147*
                  (2013.01); *H01J 49/24* (2013.01)

(56) References Cited

U.S. PATENT DOCUMENTS

| | | |
|---|---|---|
| 2006/0016983 A1 | 1/2006 | Kobayashi |
| 2010/0200746 A1 | 8/2010 | Osgood et al. |
| 2011/0006201 A1* | 1/2011 | Correale .............. G01N 1/2202 250/288 |
| 2011/0006202 A1* | 1/2011 | Correale .............. G01N 1/2202 250/288 |
| 2017/0168030 A1* | 6/2017 | Mensa ................ G01N 30/722 |

* cited by examiner

PORTABLE ELECTRONIC DEVICE FOR THE ANALYSIS OF A GASEOUS COMPOSITION

CROSS-REFERENCE TO RELATED APPLICATIONS

This application is a National Stage entry of International Application No. PCT/IB2015/054992 filed on Jul. 2, 2015, which claims priority to Italian Patent Application No. MI2014A001228 filed on Jul. 7, 2014. The disclosures of the prior applications are hereby incorporated in their entirety by reference.

TECHNOLOGICAL BACKGROUND OF THE INVENTION

Field of Application

This invention relates to the field of electronic devices for the analysis of a gas composition, based on the control of gaseous flows, and on a generation and control of ion flows.

The invention likewise includes methods of analysis of a gas composition present in the environments to be analyzed, for example, industrial process environments.

Description of the Prior Art

Numerous systems and devices are known for the analysis of the gas composition of a gaseous flow, for example analytical systems employing mass spectrometers.

These known systems act "a posteriori", with respect to a process with generation of is gas to be analyzed, since they typically operate on gaseous flows, injected in them, coming from the environment to be analyzed.

Moreover, these known systems operate by means of an ionization of gas flows, which requires an ionization environment maintained at vacuum pressures (i.e., below 1 mbar, and preferably around $10^{-3}$ mbar). For this reason, such systems must be equipped with bulky and expensive pumping means, suitable to extract from the ionization environment a large part of the flows injected for analysis, to create the vacuum conditions necessary for ionization. Therefore, the analysis is performed on gaseous residues that remain in the ionization environment, obtained by subtraction from the injected flows.

The known systems mentioned above have various drawbacks.

First of all, they are relatively expensive and bulky, for the reasons explained above: in fact, they may more properly be referred to as "systems" and not "devices".

In addition, the precision of the analysis depends on the fidelity with which the gas composition to be analyzed is represented by the vacuum-pressure gaseous residues obtained as a result of the pumping. Such precision may be inadequate for most applications, possibly requiring complex procedures and systems for correction and adjustment.

Finally, in these known solutions, it is not possible to improve the precision of the analysis, while the analysis is being performed, by enriching, in a controlled manner, the gas composition to be analyzed.

On the other hand, in a growing number of important applications, the need emerges to have devices for the analysis of gaseous flows that are compact, portable and inexpensive and also precise and reliable, so "top-of-the-line".

This can be advantageous, for example, for the analysis of gas compositions in an industrial environment, or for the analysis of discharge gas of an industrial process, downstream of the process, and without interfering with it.

It is also clearly desirable to have gas analysis devices that, while ensuring sufficient precision and reliability, are increasingly miniaturized and compact, which would considerably enlarge the field of application, to the point of, ideally, achieving miniaturized "gas composition sensors" installable in cars, airplanes, pollution detection controllers and so on.

As illustrated above, the known systems for gaseous analysis are not able to meet the above-mentioned desired requirements or the above-mentioned needs.

In light of the above, the object of this invention is that of devising and making available a device for analyzing gaseous flows, and related methods, employing such a device, that are improved so as to meet the above-mentioned needs, and that are able to overcome, at least partially, the drawbacks described above with reference to the known art.

SUMMARY OF THE INVENTION

This scope is achieved by a device according to claim 1.

Additional embodiments of the device are defined in the dependent claims 2 to 15.

A gaseous flow analysis method, carried out by using the device of the invention, is defined in claim 16.

A further embodiment of such a method is defined in dependent claim 17.

An industrial process analysis method, carried out by using the device of the invention, is defined in claim 18.

BRIEF DESCRIPTION OF THE DRAWINGS

Further characteristics and advantages of an electronic device for analyzing gas composition, according to this invention, and methods using such a device, will result from the following description of preferred embodiments, provided as non-limiting examples, with reference to the accompanying figures, wherein.

DETAILED DESCRIPTION

Figure 1:
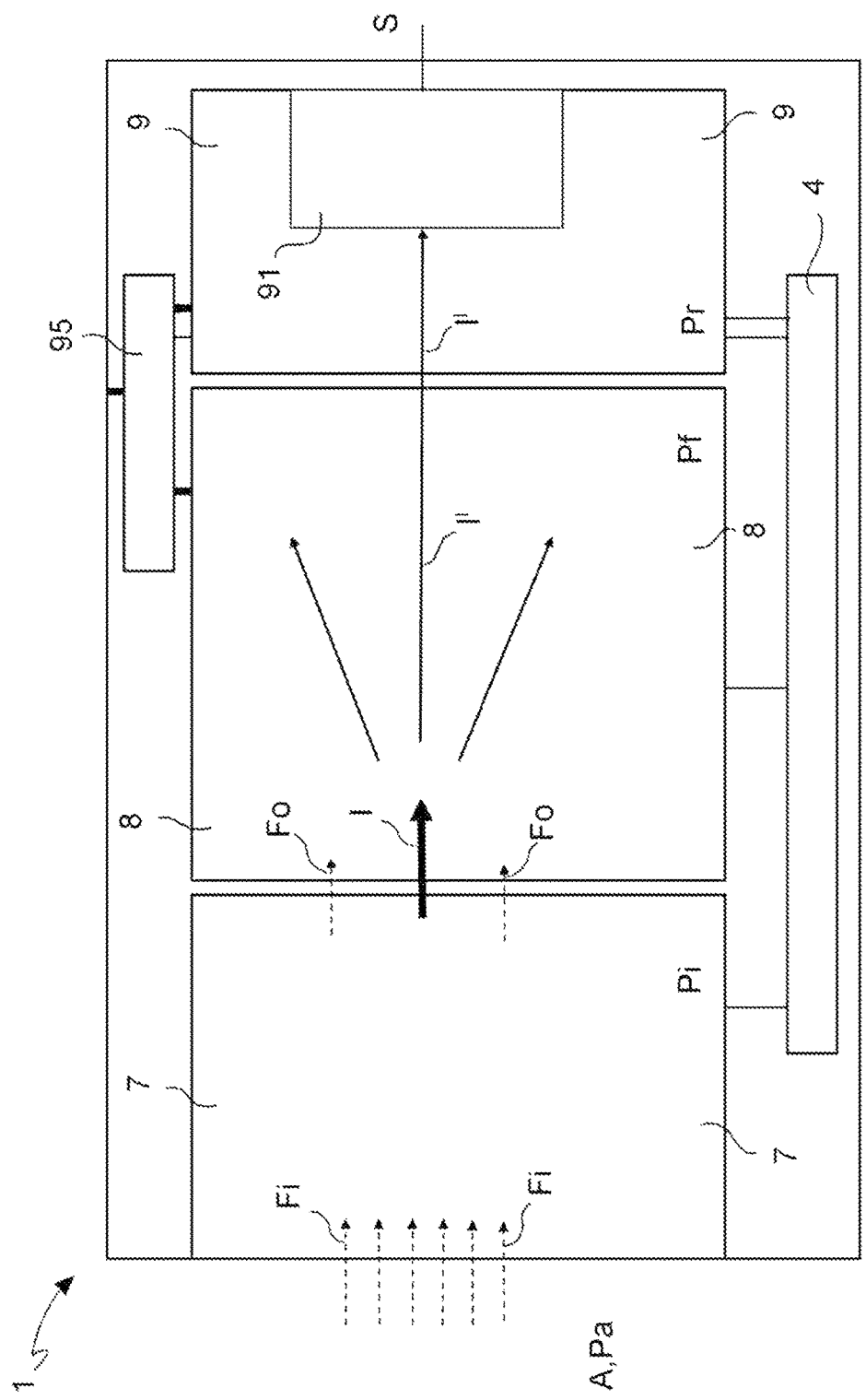
FIG. 1 is a simplified functional diagram of the device according to the invention.
Figure 2:
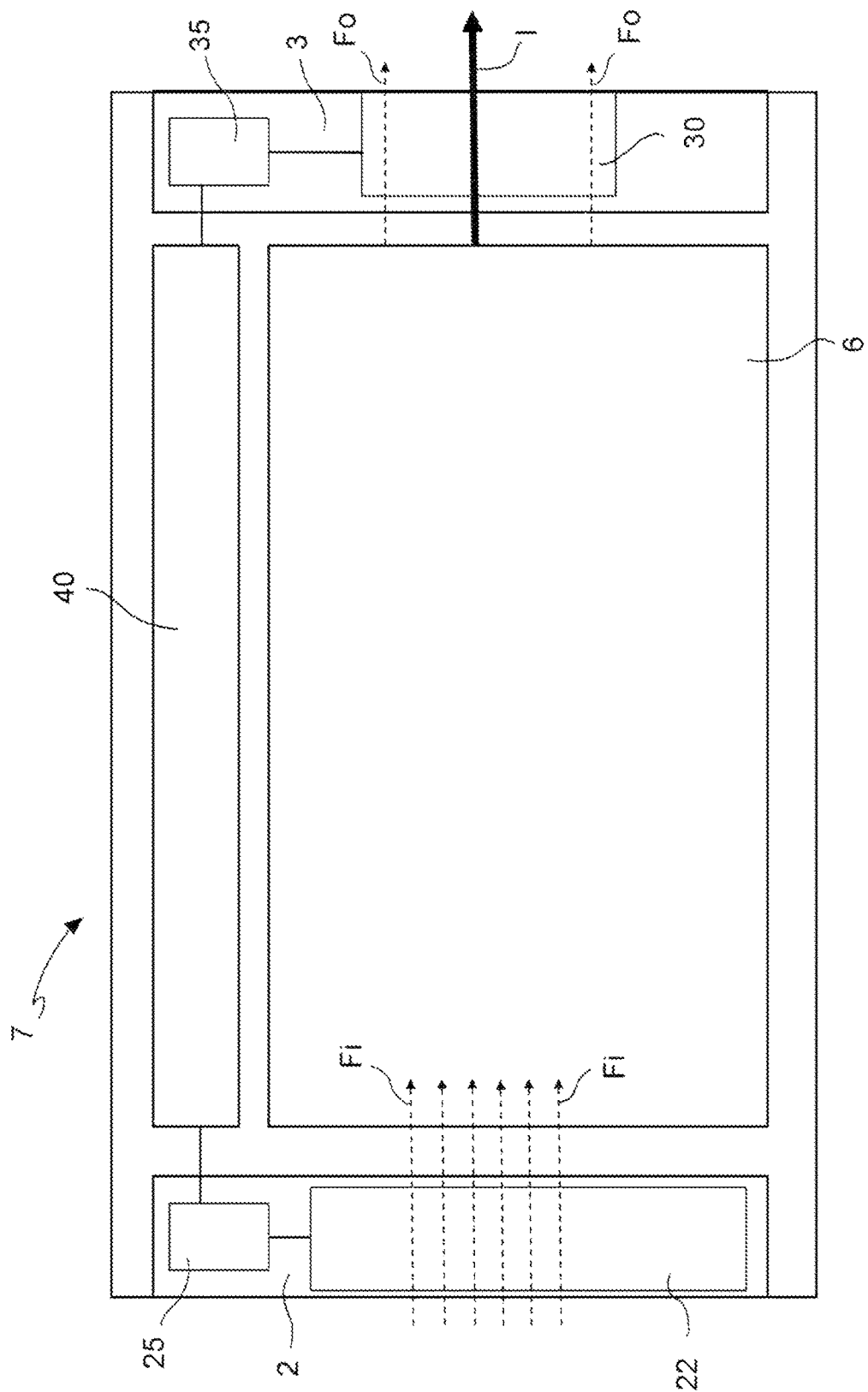
FIGS. 2-6 illustrate portions of a sampling module comprised in an embodiment of the device.

With reference to FIGS. 1-13, and in particular to FIG. 1, there is described an electronic device 1 for analyzing of a gaseous composition (i.e., a gas composition) present in an environment A, at an environment pressure Pa.

The device is portable and can be placed in such an environment A, and comprises a gas sampling module 7, an ion filtering module 8 and an ion detecting module 9.

The sampling module 7 is configured to adjust an input gaseous flow Fi of gaseous particles from the environment A and an output gaseous flow Fo so as to reproduce inside is the sampling module 7 a gaseous composition representative of the gaseous composition to be analyzed. In addition, the sampling module 7 is configured to ionize said gaseous particles and to emit the ions produced, so as to generate an ion flow I having an ion composition representative of the gaseous composition to be analyzed.

The ion filtering module 8 is operatively connected to the sampling module 7 to receive the ion flow I, and is configured to controllably select at least one type of ions present in the ion flow I and to generate a corresponding at least one homogeneous ion beam I', having an intensity representative of the concentration of the corresponding gas particle in the gaseous composition to be analyzed.

The ion detecting module 9 is operatively connected to the ion filtering module 8 to receive at least one ion beam I', and is configured to measure the intensity of such at least one ion beam I' and to generate a corresponding electric signal S representative of the concentration of the corresponding gas particle in the gaseous composition to be analyzed.

The device 1 also comprises pumping means 95, configured to pump gas from the device 1, so as to control an ionization pressure Pi that is present inside the sampling module 7.

The sampling module 7 is configured in such a way that the input gaseous flow Fi comprises a plurality of micro-flows at a molecular or predominantly molecular regime, at the environment pressure Pa, and the output gaseous flow Fo is a flow at a molecular or predominantly molecular regime, at the ionization pressure Pi.

According to an embodiment, the device 1 is an integrated device.

The environment pressure Pa, in which the device 1 can operate, is the most varied; typically, it may be an atmospheric pressure (about 1 atm) or higher.

In a typical example embodiment, the above-mentioned ionization pressure Pi, maintained within the sampling module 7, is a vacuum pressure.

In particular, the ionization pressure Pi may be between $10^{-2}$ mbar and $10^{-6}$ mbar.

According to an implementation option, the filtering module 8 and the ion detecting module 9 are maintained at a pressure lower than, or equal to, the ionization pressure Pi.

According to a preferred implementation option, the device 1 is configured to maintain an ionization pressure Pi in the sampling module 7 in the range between $10^{-2}$ mbar and $10^{-5}$ mbar; a filtering pressure Pf, in the filtering module 8, lower than the ionization pressure, and typically in the range between $10^{-5}$ and $10^{-7}$ mbar; and a detecting pressure Pr, in the detecting module 9, lower than the filtering pressure, and typically in the range between $10^{-6}$ and $10^{-8}$ mbar.

With reference to the input gaseous flow Fi and output gaseous flow Fo, it should be noted that, according to a commonly used nomenclature, the terminology "flow at a molecular regime," means a gaseous flow in which the mean free path A of a gaseous particle (i.e., of a gas molecule) is comparable to, or larger than, the dimensions D of the channel or container in which it is located, due to which the path of each particle is nearly free and independent with respect to that of the other particles.

The commonly accepted definitions, regarding the classification of flows, agree in defining as "flow at molecular regime" a flow in which the parameter D/λ is comparable to, or less than, 1.

Moreover, a "flow at a predominantly molecular regime" is defined as a flow in which the parameter D/λ is of the order of magnitude of a few units (for example, conventionally, <10): in fact, in such conditions, although collisions between particles are not, strictly speaking, reduced to zero, most of the particles are in molecular regime conditions for most of the time.

The book "*Vacuum Technology*" by A. Roth, NHPC, 1976, Chapters 2 and 3, for example, can be considered as an authoritative theoretical reference on the subject.

Obviously, the mean free path A also depends on the conditions of pressure and temperature; in particular, it is directly proportional to the temperature measured in Kelvin and is inversely proportional to the pressure. Assuming that the significant use conditions of valve systems are at ambient temperature conditions (for example in a range between 273° K and 313° K), or at a different temperature, as long as substantially constant, the pressure results to be the essential parameter.

In conditions of vacuum pressures (for example, below 1 mbar) and even more of high vacuum (for example, below $10^{-3}$ mbar) it is possible to obtain flows at a predominantly molecular regime even through channels of millimetric, or higher, dimensions.

On the contrary, in the other, non-vacuum, pressure conditions and, in particular, at atmospheric pressure or higher, it is necessary to reduce the dimensions of the channels to sub-micrometric values.

According to an embodiment, as illustrated in FIGS. 2-7, the sampling module 7 comprises an ionization chamber 6, an inlet member 2 and an ion outlet member 3.

The ionization chamber 6 is suitable to be kept at the ionization pressure Pi and is configured to contain and ionize the gas particles present therein.

The inlet member 2 is configured to inhibit or allow and/or adjust an inlet in the ionization chamber of a gaseous flow Fi. The inlet member 2 comprises a gaseous flow adjusting interface 22 having a plurality of nano-holes 20, having sub-micrometric (i.e., sub-micrometer) dimensions, suitable to be opened or closed in a controlled manner, to inhibit or allow the plurality of micro-flows at a molecular or predominantly molecular regime.

The ion outlet member 3 is operatively connected to the ion filtering module 8 and is configured to inhibit or allow and/or adjust the output gaseous flow Fo, at a molecular or predominantly molecular regime, and the ion flow I of the generated ions.

According to an embodiment option, the outlet member 3 comprises an orifice 30, suitable to be opened or closed in a controlled manner, so as to control an output conductance for the output gaseous flow Fo.

Figure 3:
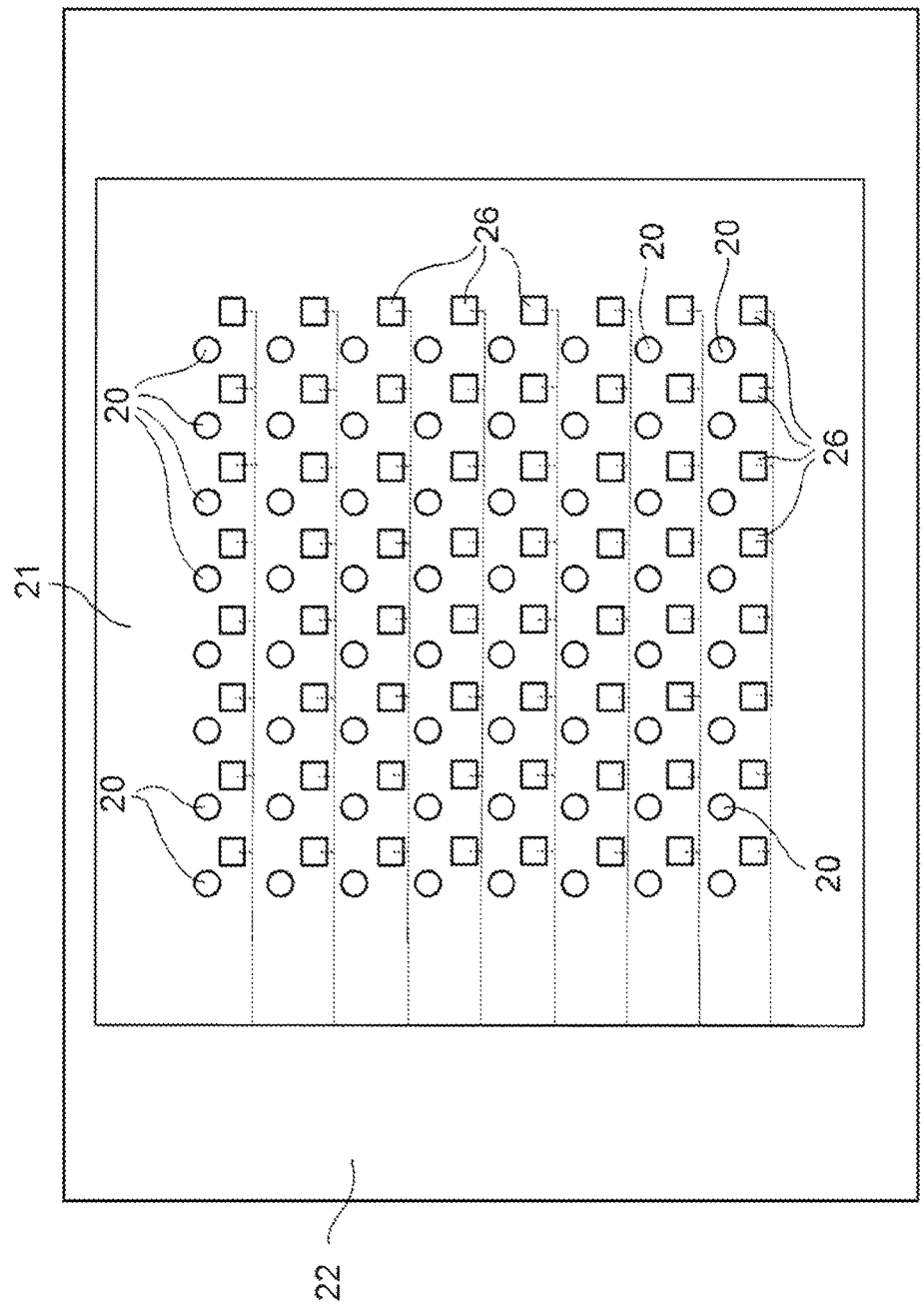
Figure 4:
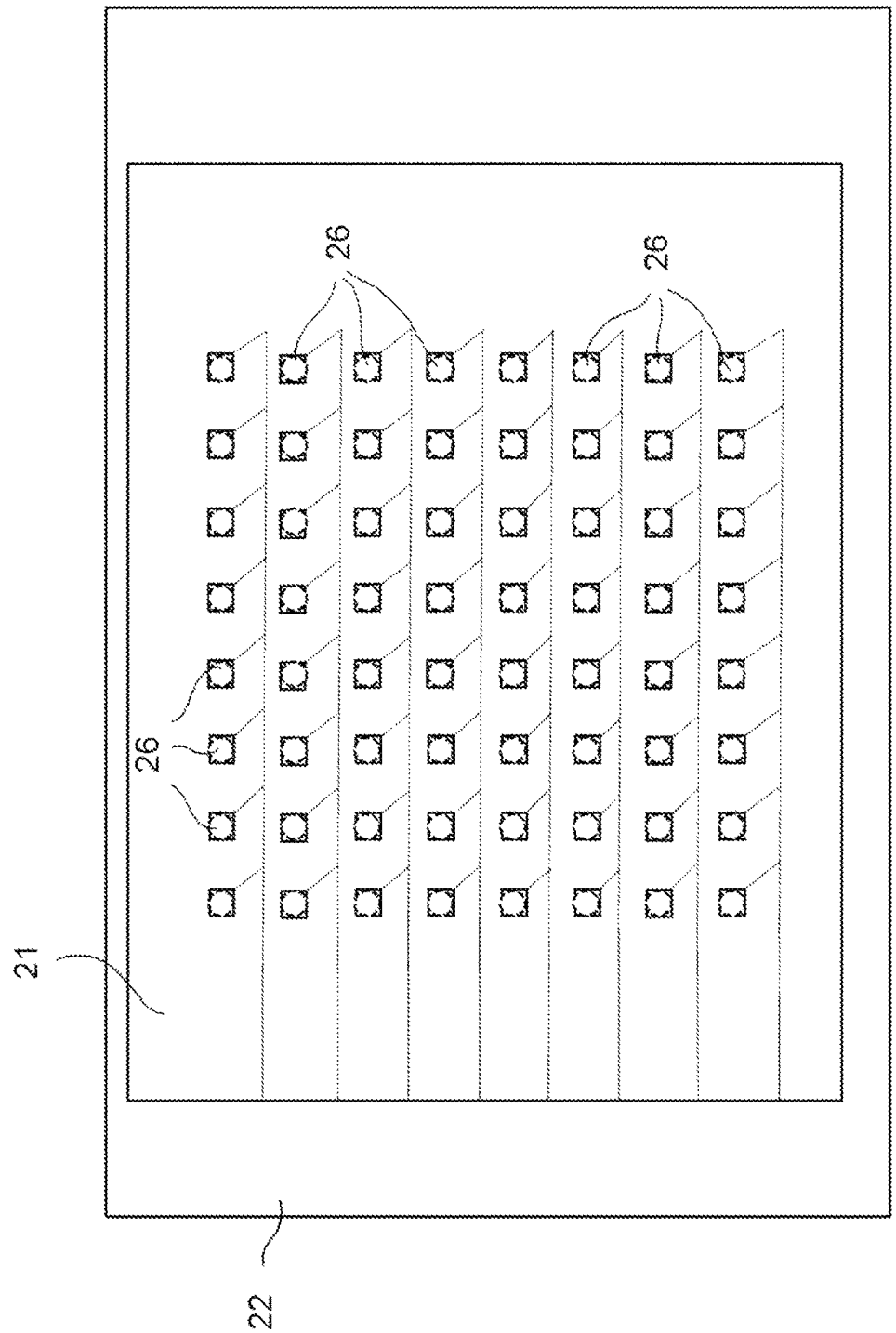
Figure 5:
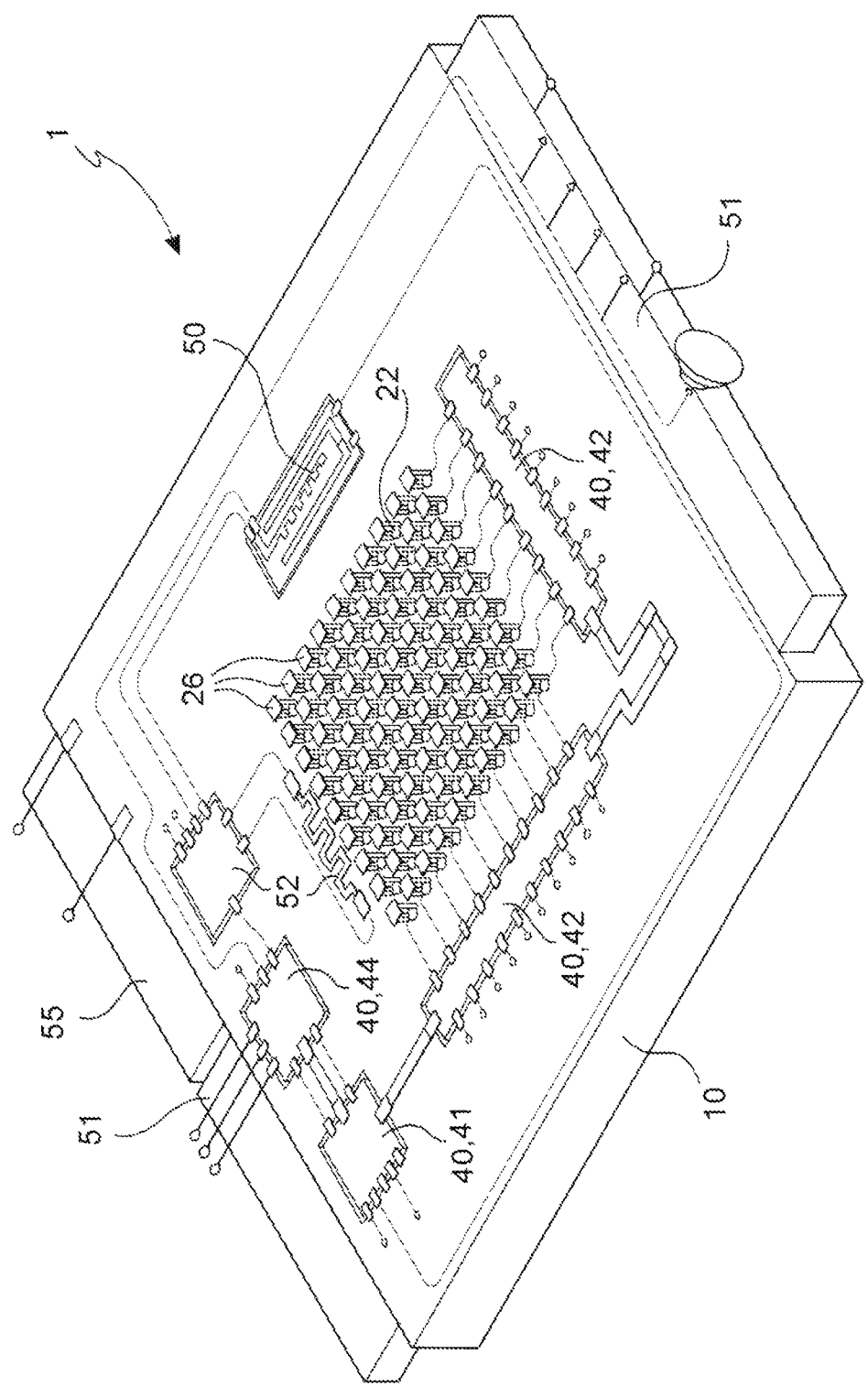

FIGS. 3, 4 and 5 illustrate the adjusting interface 22 of the inlet member 2 of the sampling module 7.

According to an implementation example, each nano-hole 20 is configured to allow micro-flows between $10^{-8}$ and $10^{-6}$ mbar·l·sec$^{-1}$. In this way, the adjusting interface 22 can control gaseous flows with an accuracy and a very fine granularity, equal to one of these micro-flows. Other flow values are of course possible, depending on the dimensions with which the nano-holes are made, and on the pressure gradient to which the nano-holes are subjected.

The fact that the flow adjusting interface allows a passage of gas exclusively through the nano-holes of sub-micrometric dimensions is enabling with respect to the functionality of allowing flows at a molecular or predominantly molecular regime. In fact, it can be calculated that, within a very wide temperature range that covers all conditions of reasonable use, and for almost every type of gas, channels of sub-micrometric diameter allow obtaining the desired values of D/λ (less than 10, in any case, and preferably comparable to 1 or lower) even at atmospheric or higher pressures.

Advantageously, the specific dimension chosen, within the sub-micrometric interval, for the nano-holes of a specific embodiment of the device, can take into account of the pressure conditions specified in the conditions of use.

The sub-micrometric dimensions of each nano-hole imply that the diameter of the nano-hole (i.e., the dimension on a plane substantially perpendicular to the flow) is of the order of magnitude of hundreds of nanometers or less.

According to an implementation example, each nano-hole 20 has a diameter in the range from 10 to 100 nm, and preferably between 20 and 100 nm. Other values (for example between 50 and 500 nm) are possible, depending on the design specifications of the device.

According to an implementation example, the nano-holes are formed in a membrane 21, having a thickness of the order of hundreds of nanometers (nm) or lower (thus, typically an order of magnitude comparable to that of the diameter), and preferably between 50 and 500 nm.

According to a preferred embodiment, each nano-hole 20 has a defined geometry and a deterministically measurable conductance, the conductance being a parameter that quantifies the micro-flows that can pass through the nano-hole.

Preferably, the geometry of the nano-holes 20 is substantially cylindrical.

In the embodiment described above, each nano-hole is approximately a cylinder, or tube, having a diameter of the order of tens or hundreds of nm, and a height of the order of hundreds of nm.

According to various implementation examples covered by the invention, the distribution, number and size of the nano-holes 20, formed in a membrane 21 of the adjusting interface 22 can be the most varied. The adjusting interface 22 can thus comprise nano-holes 20 of all equal sizes, or different from each other, in any combination.

The number of nano-holes 20 of the adjusting interface 22 can vary from several tens to several hundreds, or even thousands. This advantageously allows obtaining flows of significant intensity, even if formed by micro-flows, by opening all the nano-holes.

The arrangement of the nano-holes 20 on the adjusting interface 22 can be the most varied.

According to a preferred implementation example, the nano-holes 20 are arranged in a two-dimensional array of rows and columns.

According to an implementation option, the adjusting interface 22 comprises one or more flow control windows, each window comprising a membrane 21, through which the nano-holes 20 are derived.

Each membrane 21 can be planar or non-planar.

In a typical implementation example, the membrane 21 is planar, substantially rectangular or square, with sides of dimensions of the order of tens of micrometers, and is able to contain a number of nano-holes of the order of hundreds.

It should be noted that the adjusting interface 22, with a membrane 21 and any predetermined arrangement of nano-holes having the desired dimensions and geometries, can be obtained by techniques, in themselves known, for manufacturing membranes with holes of sub-micrometric dimensions.

Such techniques are known, for example, in the context of nano-technologies for the production of membranes for chemical-biological applications. Another example of usable techniques involves the use of silicon membranes that are perforated, in a controlled manner, by a SEM (Scanning Electron Microscope) equipped with a FIB (Forced Ion Beam) module. In this way, nano-holes of the type described above (in literature sometimes also called "nano-orifices" or "nano-pores") can be formed on the silicon membrane, as shown for example in the scientific papers: Lo, Aref, Bezryadin "*Fabrication of symmetric sub-5 nm nano-pores using focused ion and electron beams*" (Nanotechnology 17(2006)3264-3267); and Stein et al., "*Ion Beam Sculpting Time Scales*" (Physical Review Letter, vol. 89, no. 27, Dec. 30, 2002).

According to an implementation option, the sampling module 7 further comprises first actuating means 25, second actuating means 35 and sampling module control means 40.

The first actuating means 25 comprise a plurality of miniaturized nano-hole opening/closing members 26, each miniaturized opening/closing member 26 being suitable to open or close a corresponding nano-hole 20, so as to maximize or minimize, respectively, the nano-hole 20 conductance.

In a particular implementation example, each miniaturized nano-hole opening/closing member 26 is configured to hermetically seal the respective nano-hole 20, reducing to zero its conductivity, or to fully open the nano-hole 20, allowing a flow of gas through it. The property of "hermetic" closure can be defined in the design stage in relation to the size of gaseous molecules whose flow must be controlled.

The second actuating means 35 comprise a shutter 36, configured to completely close, or to keep completely open, or partially occlude, in a controlled manner, the orifice 30 of the ion outlet member 3.

The sampling module control means 40 (for example a processor 40) are configured to control the first 25 and second 35 actuating means.

The most varied ways of actuating the nano-holes are made possible by the structure of the sampling module 7, illustrated here.

In fact, the control means 40 are configured to control the gas flow Fi passing through the adjusting interface 22 by determining the pattern of open and closed nano-holes 20 in terms of the number and position of open and closed nano-holes, and/or by determining the ratio of the opening time and closing time of the nano-holes 20, or of the duty cycle.

In a preferred example embodiment, able to offer a maximum flexibility of use, the control means 40 are configured to control the inlet actuating means 25, so that each nano-hole 20 can be opened or closed individually and in an independent manner with respect to the other nano-holes 20.

According to an alternative example, the control means 40 are configured to control the actuating means 25, so as to selectively open or close one or more groups of nano-holes 20, comprising, for example, sub-sets of nano-holes adjacent to each other in an array. In is this case, the nano-holes of each sub-set can be open or closed, independently of the opening/closing of the nano-holes of the other sub-sets.

According to another example, the nano-holes 20 are all open or all closed, collectively.

By virtue of the above, the sampling module 7 provides control of inlet flows in which any combination, pattern and/or arrangement of open or closed nano-holes is possible: for example, with nano-holes all opened (as shown in FIGS. 3 and 5) or with nano-holes all closed (as shown in FIG. 4) or with some nano-holes opened and others closed. Furthermore, the combination, pattern and/or arrangement of opened or closed nano-holes can be dynamically changed over time in a desired manner.

According to possible implementation options, the inlet actuating means 25 are actuated electro-mechanically or electro-magnetically.

According to an embodiment option, illustrated in FIG. 5, each miniaturized opening/closing member 26 comprises a plug 26 electro-mechanically actuatable to close or open the corresponding nano-hole 20, through an axial movement with respect to the nano-hole 20.

According to another embodiment option, each miniaturized closing/opening member comprises a micro-cantilever, electro-magnetically actuatable, having, at an oscillating end, a substantially conical tip, suitable to be inserted in or extracted from the nano-hole.

According to a still further embodiment option, each miniaturized closing/opening member comprises a cylinder, having a diameter substantially equal to that of the corresponding nano-hole, the cylinder being electro-magnetically actuatable to be inserted in, or extracted from, the corresponding nano-hole, through an axial movement with respect to the nano-hole.

The options described above provide for an individual and independent actuation of each nano-hole.

For applications in which a collective actuation of the nano-holes is sufficient, a further embodiment option provides that the inlet actuating means 25 comprise a multiple opening/closing oscillating planar member, configured to concurrently open/close all the nano-holes 20 of the adjusting interface 2.

In this case, the single miniaturized nano-hole opening/closing members can be arranged on one side of the planar member in a configuration corresponding to that of the nano-holes, so that each miniaturized opening/closing member is simultaneously inserted into, or extracted from, the corresponding nano-hole, upon a corresponding movement of the is planar member.

According to an implementation example, the inlet actuating means 25 are arranged on a side of the adjusting interface 22 and are configured to open/close the opening of each nano-hole 20 corresponding to that side.

According to an alternative implementation example, such inlet actuating means 25 (or at least parts of them) are arranged on both sides of the adjusting interface 22, and are configured for opening/closing both openings of each nano-hole 20, corresponding to both sides of the adjusting interface 22, i.e., both ends of the tubular micro-channel formed by the nano-hole. In this case, each miniaturized nano-hole opening/closing member 26 is configured to penetrate into the nano-hole 20, in conditions of closure, entering from the respective side.

Advantageously, the miniaturized opening/closing members 26 are also suitable (or configurable) for cleaning and clearing each nano-hole 20 of possible obstructions (due, for example to molecular mono-layers that can be deposited), upon each operative event of closure and subsequent opening or upon specific anti-obstruction closing/opening events. This property is important to allow the use of the device in the most various environments, including environments of industrial processes with pollutants.

Figure 6:
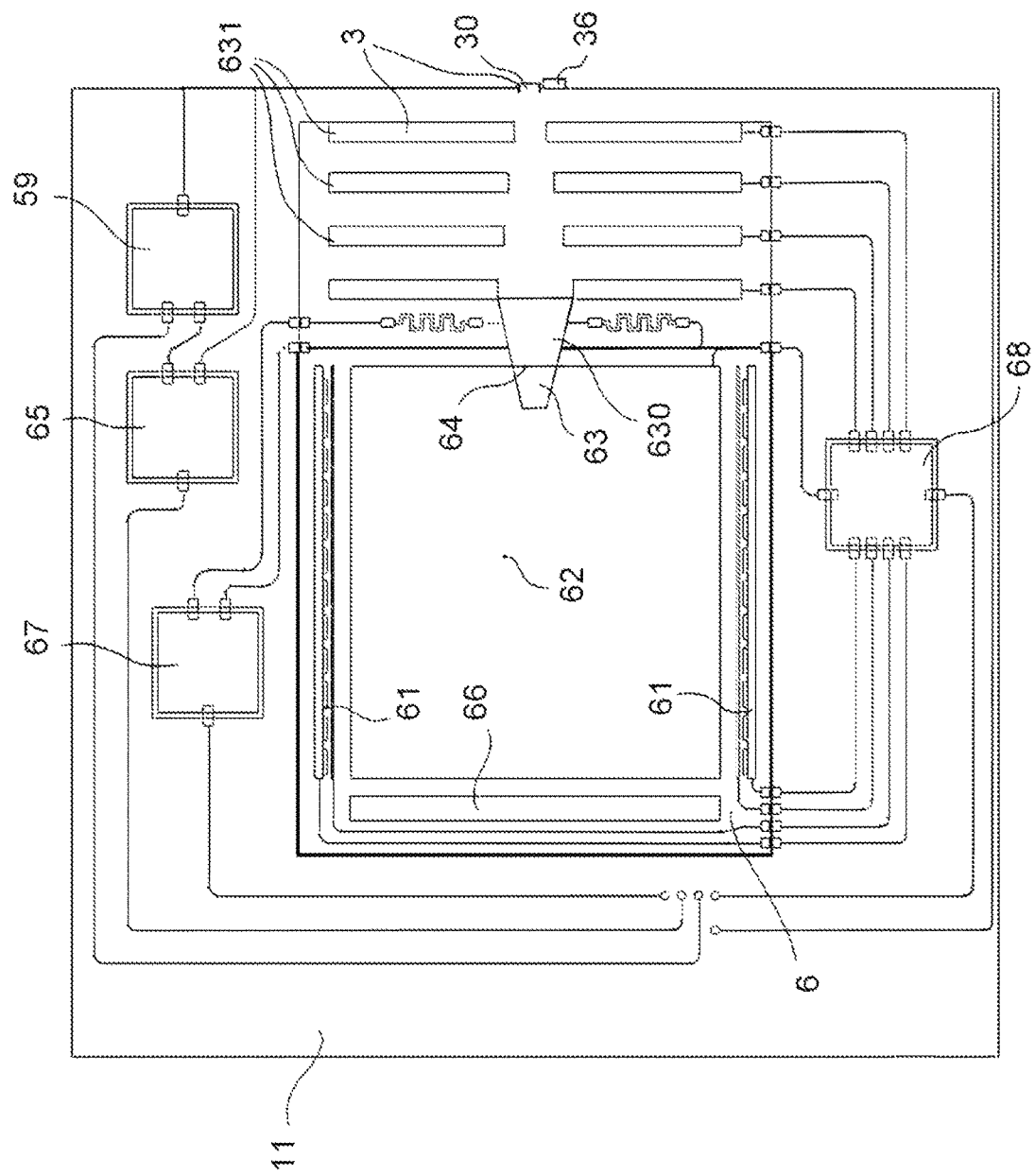
Figure 7:
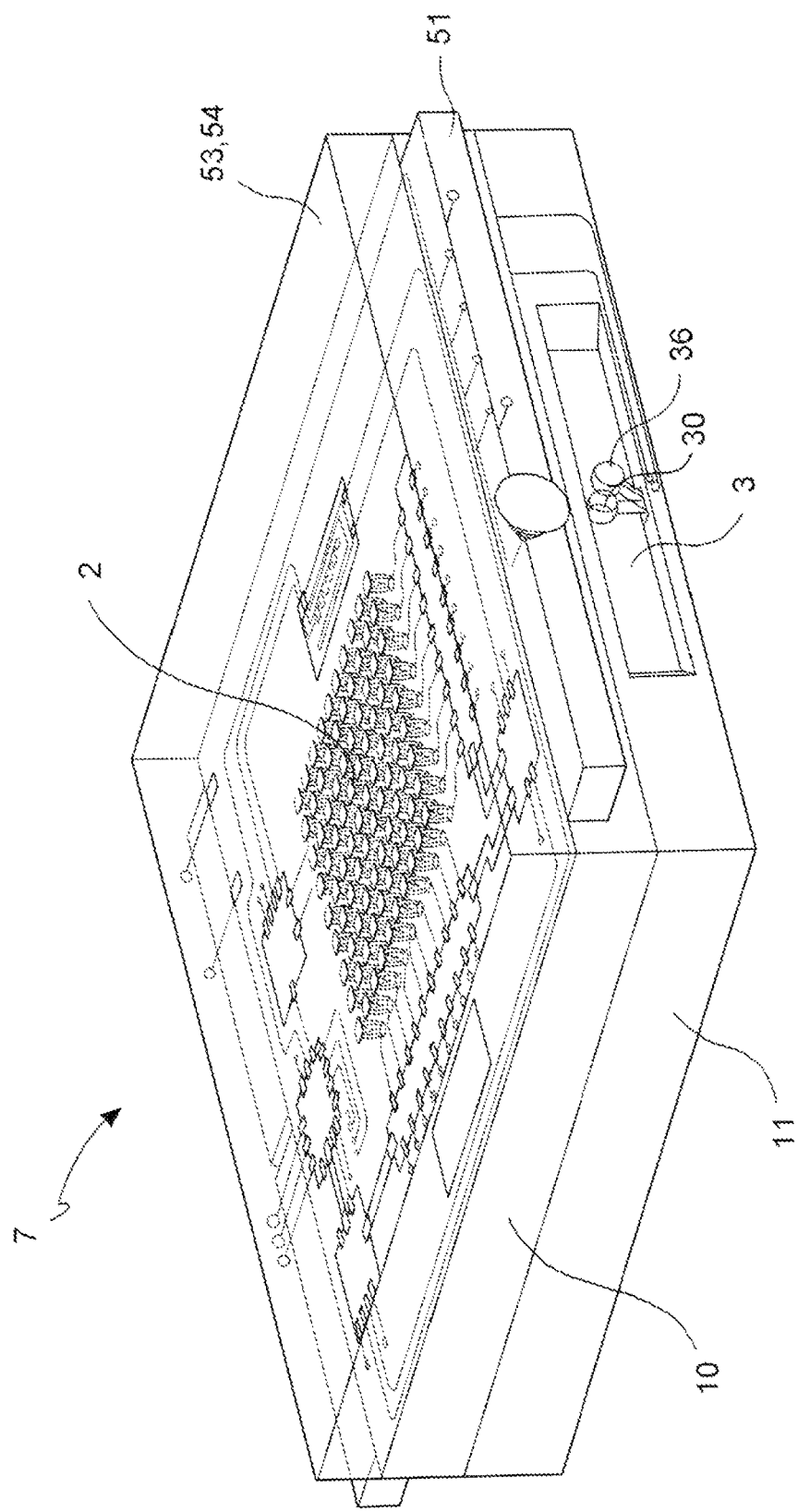
FIG. 7 is a perspective view of such a sampling module.

Now, the outlet member 3, visible for example in FIGS. 6 and 7, is considered. In an implementation example, the outlet member 3 is further configured to control and/or modulate over time the intensity of the output ion flow I.

For this purpose, the movement of the shutter 36 can be controlled electro-mechanically, by the processing means 40, so that the shutter 36 takes an opening position, in which it keeps fully open the orifice 30, or a closure position, in which it keeps the orifice 30 hermetically closed, or a plurality of intermediate positions, which determine a corresponding plurality of conditions for the opening or partial occlusion of the orifice 30.

In addition, it is also possible to drive the shutter 36 with a periodic opening/closing cycle according to a desired duty cycle.

In the example illustrated in FIG. 7, the shutter 36 has a pendulum shape.

According to an implementation option, the outlet actuation means 35 are configured to control the output gas flow Fo through an adjustment of the size of the opening of the orifice 30, and to control the modulation of the outlet ion flow I through an adjustment of the duration of closing and opening periods of the orifice 30, or of an opening/closing cycle time of the orifice 30.

Furthermore, the outlet actuation means 35 are also configured to contribute to control the pressure in the ionization chamber 6 by adjusting the duration of closure and opening periods of the orifice 30, or a closure/opening cycle time of the orifice 30, for example according to a suitable oscillation frequency.

According to a particular implementation example, the control means 40 are configured to control the intensity of the outlet ion flow I by acting on the pressure in the ionization chamber and/or on the generation of electrons by the ionization source 61.

According to another implementation example, the at least one outlet member 3 is further configured to measure the intensity of the outlet ion flow I. For this purpose, the shutter 36 can be equipped with a meter of the intensity of the ion beam, or be part of such intensity meter.

Wth reference now to FIG. 6, further details regarding the ionization chamber 6 of the device 1 will be illustrated.

In an embodiment, the ionization chamber 6 comprises ionization chamber control means 65, and further comprises at least one ionization source 61 (for example, a source of electrons).

The ionization chamber 6 then comprises an ionization region 62, containing gas particles entering through the adjusting interface 22, and is arranged so as to ionize the gaseous particles contained in it, for example by being crossed by electrons generated by the ionization source 61, so that the ionization electrons ionize such gaseous particles (i.e., gaseous molecules), thus generating respective ions (i.e., ionized molecules).

The Ionization chamber 6 also comprises first ion extraction means 63, configured to determine a preferred trajectory for the generated ions, passing through at least one first ion extraction window 64, through which the ions exit the ionization region 62, and to subsequently guide the ions toward the outlet member 3. For this purpose, the ions extraction means 63 comprise generators of time- and spatially-controlled electric and/or magnetic field.

The ionization source 61 may be an electron emission source, in itself known, such as, for example, an EI (Electron Ionization) source, in particular a field-effect "cold" emission source, such as a nano-tube source or plasma source, or by means of laser ionization.

According to an implementation example illustrated in FIG. 7, the ion extraction means 63 comprise at least one extractor and/or an ion guide 630, in itself known, to extract the ions from the ionization region 62; and further comprise at least one electrostatic lens 631, configured to define a path for the ions from the ion extraction window 64 to the orifice 30 of the outlet member 3 and to generate a collimated ion beam I as output flow.

Considering now the sampling module, with the structural aspects described above, it is evident that the sampling module control means 40 can be configured, according to what has been previously illustrated, to achieve the functional purposes of the device.

In particular, the fact that both the inlet flow and the outlet flow Fo are at a molecular or predominantly molecular regime, means that the partial gaseous concentrations, in the ionization chamber 6, reproduce the partial gaseous concentrations that are present in the external environment A to which the at least one inlet member 2 is exposed; and, therefore, the partial ion concentrations, in the output ion flow I, are deterministically representative of such partial gaseous concentrations. In particular, in the case in which the ionization cross sections of the different gaseous particles are equal or very similar, the partial ion concentrations exactly reproduce the partial gaseous concentrations. If the ionization cross sections are different, they are still deterministically known with great accuracy, whereby the partial ion concentrations may be related, again in a deterministic and precise manner, to the partial gaseous concentrations.

According to a particular implementation option, the sampling module control means 40 are also configured to vary, in a controlled manner, the ionization pressure Pi in the ionization chamber 6, by a suitable actuation of the at least one outlet member 3, so as to increase the ionization pressure Pi, based on the input flows, the volume of the ionization chamber, and an effective conductance of the output orifice (starting from a zero value up to a maximum value), which in turn depends on the opening/closing actuation times of the at least one outlet member 3.

In this option, advantageously, it is possible to "enrich" the gaseous mixture in the ionization chamber, while remaining in the pressure conditions that allow ionization. Consequently, one can increase the intensity of the ion flow I, and thus of the subsequent homogeneous ion beams I', and thus increase the signal-to-noise ratio of the electrical output signal S and, ultimately, improve the analysis accuracy and sensitivity of the device. A further improvement effect of such signal-to-noise ratio can derive results from the possibility to modulate the intensity of the ion flow I with a suitable modulation frequency or "duty cycle".

Figure 8:
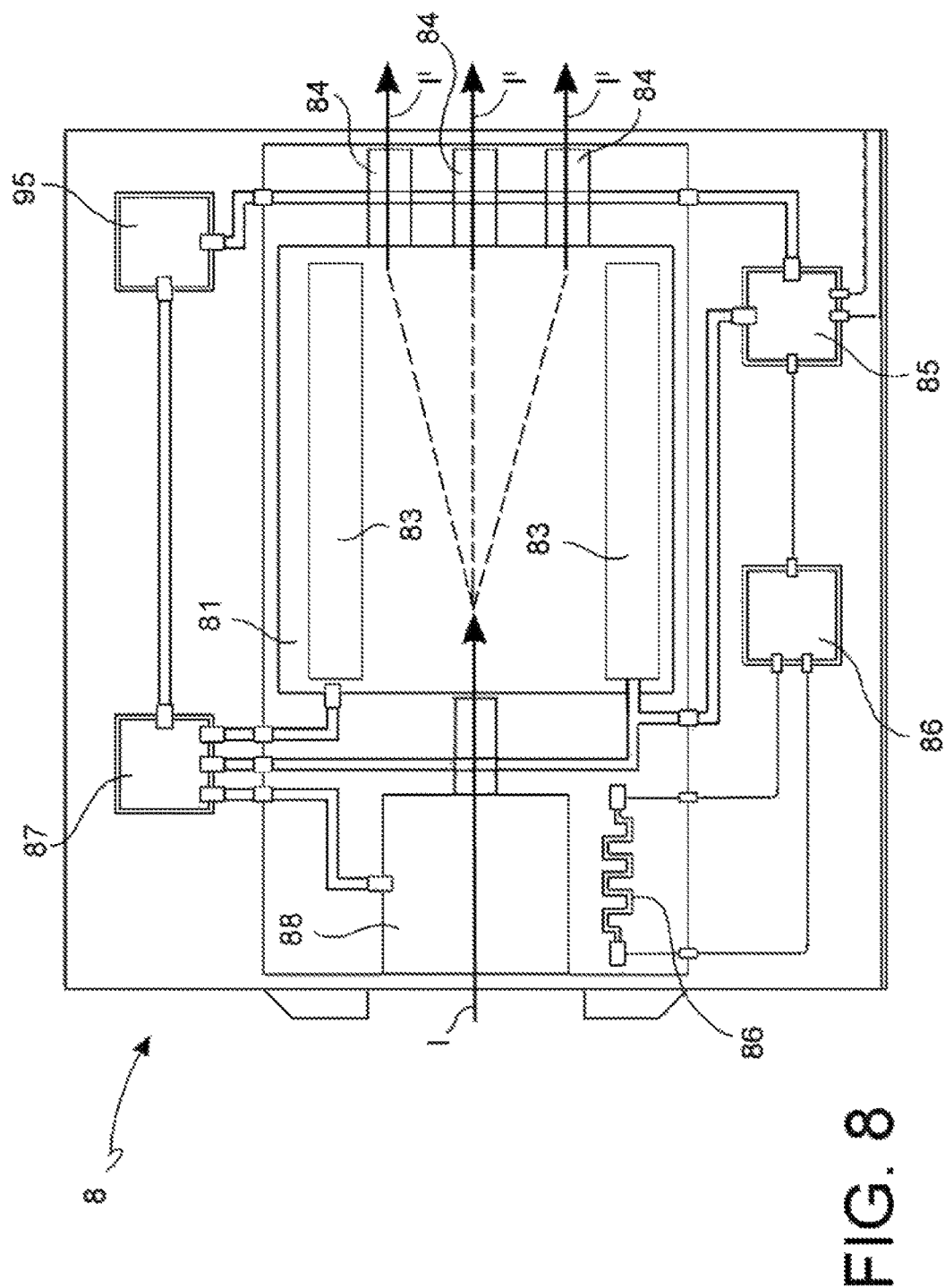
FIG. 8 presents a structural diagram of an ion filtering module comprised in an embodiment of the device.

Wth reference now to FIG. 8, the filtering module 8 is considered.

According to an embodiment, the ion filtering module 8 comprises a filtering region 81, through which the ion beam I passes in order to be filtered. The filtering region 81 comprises at least one second ion extraction window 84, through which the at least one homogeneous ion beam I' exits the filtering region 81 and the ion filtering module 8.

The ion filtering module 8 further comprises at least one electric and/or magnetic field generator 83, configured to generate in the filtering region 8 an electric and/or magnetic field and/or potential, with an amplitude and/or frequency and/or spatial pattern that is variable in a controlled manner; and also comprises filtering module control means 85, configured to control the electric and/or magnetic field and/or potential in amplitude and/or frequency and/or spatial pattern, so as to control a trajectory or a filtering region 81 passing-through speed, for the ions of the ion flow I, as a function of the respective mass thereof.

According to an implementation example, the ion flow I comprises a plurality of ions of different type, having different, respective masses, and the filtering module control means 85 are configured to select a type of ion determining a trajectory for passing through the second extraction window 84, for particles having a different mass than that of the selected ion type.

According to another implementation example, the ion flow I comprises a plurality of ions of different types, having respective different masses, and the filtering module control means 85 are configured to select one type of ion by determining a pass-through speed, for particles having a mass equal to that of the type of ion selected, for which such particles arrive at the second extraction window 84 while it is open, and instead a different pass-through speed, for particles of mass different than that of the type of ion selected, for which such particles arrive at the second extraction window 84 while it is closed (where the extraction window 84 can be implemented by means of a shutter or by electro-static means).

According to an implementation option, the ion flow I comprises a plurality of ions of different type, having corresponding different masses, and the filtering module control means 85 are configured to extract sequentially over time ions of different type, thus generating a tuneable scanning of respective homogeneous ions beams I'.

According to an implementation example, the filtering module 8 also comprises a first achromatic ion guide 88 configured to guide the received ion flow I in the filtering region 81.

In an embodiment, the ion filtering module 8 comprises a miniaturized mass filter 81, 83.

This mass filter 81, 83 may be realised, for example, by a single quadrupole mass filter, or by a multiple quadrupole mass filter with quadrupoles coupled in different combinations, or by a magnetic sector, in itself known.

In another embodiment, the ion filtering module 8 comprises an RF cyclotron filter or a "time of flight" (TOF) mass filter.

According to another implementation option, not shown in the figures, the filtering module 8 also comprises a further filtering member configured to form a chemical reaction cell, so as to distinguish ions of different chemical substances having an equivalent or similar mass.

In an implementation example, the chemical reaction cell is realised in correspondence of the above-mentioned achromatic ion guide 88.

Such an additional filter element can be arranged, for example, upstream of the filtering region 81.

According to an implementation example, the device 1 also comprises ion flow monitoring members before the entrance and after the exit of the filtering region 81.

In the example illustrated in FIG. 8, the filtering module further comprises a power supply 87, a heater 86 and a pumping member of the pumping means 95.

Figure 9:
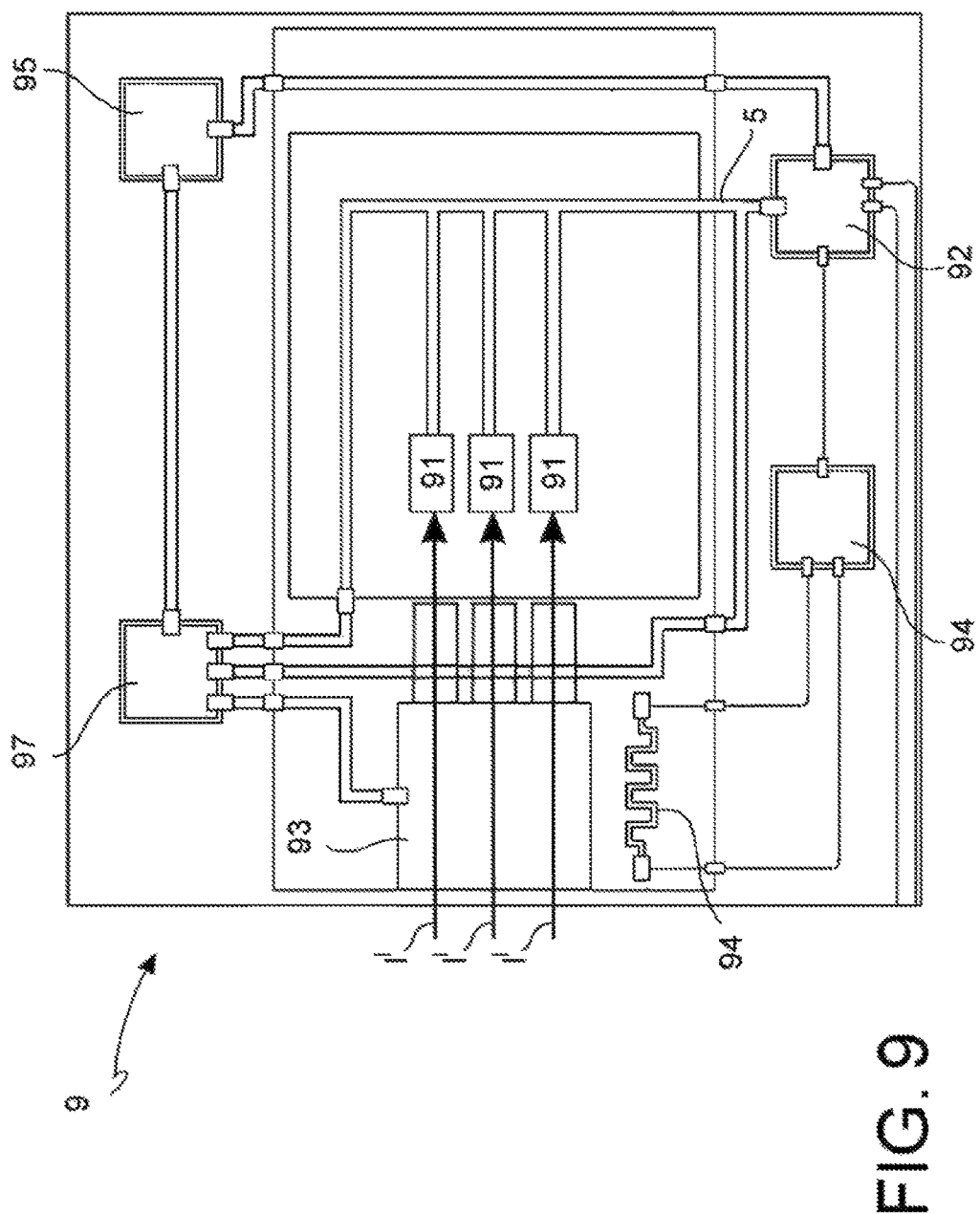
FIG. 9 presents a structural diagram of an ion detecting module comprised in an embodiment of the device.
Figure 10:
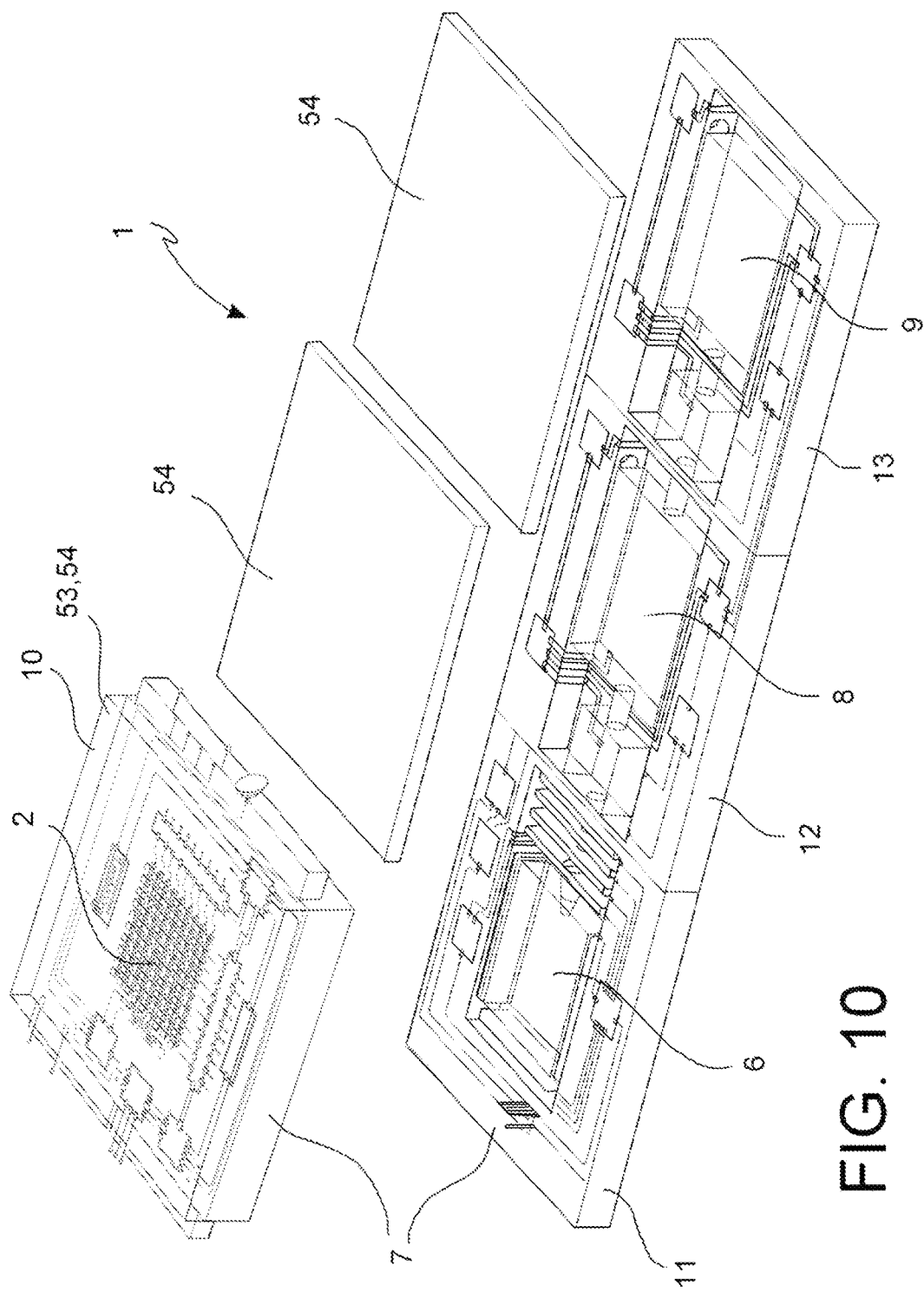
FIGS. 10 and 11 illustrate an exploded and perspective view, respectively, of an embodiment of the device.
Figure 11:
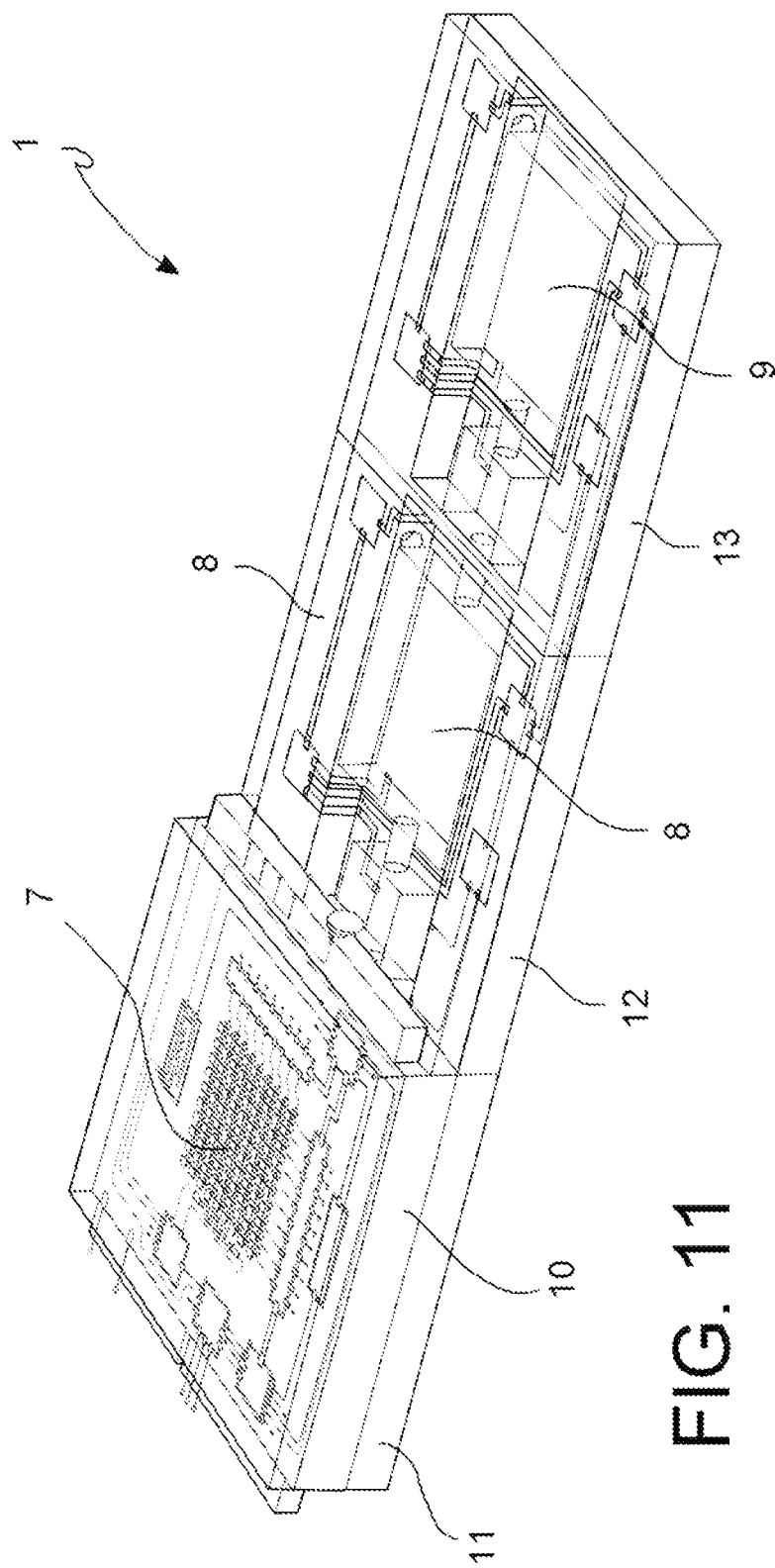

Wth reference now to FIG. 9, the ion detecting module 9 is considered.

According to an embodiment, the ion detecting module 9 comprises detecting module control means 92, and also one or more detectors 91, each configured to generate an electrical signal S proportional to the intensity of the ion beam I' incident to it.

According to various implementation options, each detector 91 is realized by a Faraday Cup, or by a discrete-dynode SEM (Second Electron Multiplier), or by a continuous-dynode Channeltron or by a detector with high-voltage sensors, in themselves known.

According to an embodiment example, the ion detecting module 9 comprises a second achromatic ion guide 93 configured to guide the one or more received ion beams I' towards a respective detector 91. In an implementation example, this second achromatic ion guide 93 can be configured to serve as a further chemical reaction cell.

In the example illustrated in FIG. 9, the ion detecting module further comprises a power supply 97, a heater 94 and a pumping member of the pumping means 95.

Advantageously, according to an embodiment, the ion filtering module 8 comprises a plurality of second extraction windows 84, and the ion detecting module 9 comprises a respective plurality of detectors 91. In addition, the ion filtering module control means 85 are configured to send in parallel different homogeneous ion beams I', corresponding to respective different types of ions, toward a respective one of the second extraction windows 84; and the ion detecting module control means 92 are configured to guide each of such homogeneous ion beams I', coming in parallel from the ion filtering module 8, toward a respective detector 91, so as to generate in parallel a plurality of electric signals S, each representative of a respective gas particle of the gaseous composition to be analyzed.

In accordance with an embodiment of the device 1, the pumping means 95 comprise at least one miniaturized pumping member and pumping control means.

According to various implementation options, each miniaturized pumping member is realized by means of an ion micro-pump, or a "getter".

According to an example embodiment, shown in FIG. 8, the miniaturized pumping member 95 is installed in the ion filtering module 8, and is configured to maintain the sampling module 7 (through the outlet member 3) at ionization pressure (Pi) conditions and both the ion filtering module 8 and the ion detecting module 9 at pressures equal to, or lower than, the ionization pressure Pi.

According to other implementation options, a second pumping member is installed in the sampling module 7 and/or a third pumping member is installed in the ion detecting module 9.

In this case, the above-mentioned pumping members are typically configured to maintain a filtering pressure Pf, in the filtering module 8, lower than the ionization pressure Pi, and typically in the range between $10^{-5}$ and $10^{-7}$ mbar; and to maintain a detecting pressure Pr, in the detecting module 9, less than the filtering pressure Pf, and within the interval between $10^{-6}$ and $10^{-8}$ mbar.

Wth reference now to further structural and functional aspects of the device, shown in FIGS. 1 and 10-13, the following aspects should be noted.

According to an embodiment, the device 1 also comprises processing means 4, such as a processor 4, operatively connected with the sampling module 7, the ion filtering module 8, the ion detecting module 9 and the pumping means 95.

The processing means 4 are configured to control the sampling module control means 40, the ionization chamber control means 65, the ion filtering module control means 85, the ion detecting module control means 92 and the pumping control means.

Furthermore, the processing means 4 are configured to receive from the ion detecting module 9 the one or more electrical signals S representative of the gaseous concentrations, and to make the related results available.

According to a further embodiment, the device 1 further comprises at least one internal pressure sensor, configured to measure a pressure value, present inside the device, and at least one further external pressure sensor 50, configured to measure a pressure value Pa of the external environment.

According to an implementation option, the device 1 comprises a plurality of internal pressure sensors, configured to detect respective pressure values inside, respectively, of the sampling module 7, the filtering module 8 and the ion detecting module 9.

According to an embodiment, the device 1 also comprises an input/output interface 51 (illustrated in FIG. 5), operatively connected to the electronic processing means 4, and configured to send outside the device, or to receive from outside the device, control and/or monitoring and/or calibration and/or diagnostic signals.

In various implementation examples comprised in the invention, the processing means 4 are configured to control the functions of the device on the basis of control signals coming from outside the device via the input/output interface 51, and/or on the basis of the pressure values measured by the miniaturized pressure sensors and/or of the current of the measured beam and/or of the measured mass spectrum.

In a further implementation example, the device 1 is configured to calibrate the results of the analysis on the basis of a comparison with reference results, obtainable by placing in communication the device 1, through a second inlet member, with a further environment in which a known gas composition is present.

Advantageously, the adjustment procedure is carried out while the device is in operating conditions and does not interfere with the results of the analysis performed by the device.

In another implementation example, the device 1 is configured to perform, in parallel, analyses of several different environments, by providing further respective inlet members faced to such environments.

Optionally, the device 1 also comprises a reference pressure sensor (not shown in the figures), encapsulated in a sealed and/or openable environment, and configured to provide a reference signal to the processing means 4 for calibration and/or diagnostic functions of the device.

According to an implementation example, the device 1 also comprises a power supply interface 55 (illustrated in FIG. 5).

According to an implementation example, the device 1 also comprises an electric power supply 68 for the ionization chamber (illustrated in FIG. 6).

The device 1 may also comprise controlled heating means, configured to maintain a desired temperature, under the control of the processing means 4.

In particular, according to an implementation option, these controlled heating means comprise at least a first heater 52 in the adjusting interface 22, at least one second heater 62 in the sampling module 7, at least one third heater 86 in the ion filtering module 8 and at least one fourth heater 94 in the ion detecting module 9.

According to a further embodiment example, the device 1 also comprises particulate filtering means 53, arranged so as to cover the entire device (for example, equipped with filters with micro-metric frame).

Furthermore, the device 1 may comprise thin protection films, configured to reduce the adsorption of process gas (for example, hydrophobic films to prevent the adsorption of moisture present in the process environment) and prevent corrosion.

It should be noted that the electronic processing means 4 can be configured to perform a diagnostic procedure of the device 1, on the basis of a processing of the data received from the pressure sensors, of measurement data of the intensity of the ion beam and/or of stored data relating to nominal predetermined operating conditions or operating environmental conditions in which the device is destined to be placed, so as to identify possible operating anomalies of the device.

In addition, the electronic processing means 4 are configured to perform, if the diagnostic procedure gives a negative result, a procedure for an adjustment and/or compensation and/or optimization of the device, by acting on operating parameters of the device to correct and/or compensate for the identified operating anomalies, based on the results of the aforesaid diagnostic procedure.

With reference now to aspects of structural implementation, it should be noted that, in an embodiment, the device 1 comprises an interface and control chip 10, in which at least the adjusting interface 22 and the first actuating means 25 of the sampling module 7 and the electronic processing means 4 are implemented. The device 1 then comprises at least one processing chip, in which the ionization chamber 6, the ion outlet member 3, and the second actuating means 35, of the sampling module 7, and moreover the ion filtering module 8, the ion detecting module 9 and the second pumping means 95 are implemented. In such a case, the interface and control chip 10 overlaps the at least one processing chip, so that the corresponding portions of the sampling module 7 match, and, furthermore, the interface and control chip 10 is connected to the at least one processing chip 11 so as to ensure a vacuum seal and to form with it a single integrated device.

In the embodiments illustrated in FIGS. 10-13, the device 1 comprises, in particular, three processing chips 11, 12, 13.

The ionization chamber 6, the ion outlet member 3, and the second actuating means 35, of the sampling module 7, are implemented in the first processing chip 11. The ion filtering module 8 is implemented in the second processing chip 12. The ion detecting module 9 and the pumping means 95 are implemented in the third processing chip 13.

The three processing chips 11, 12, 13 are mutually connected in a vacuum sealed manner, so as to allow a passage of ions from the ion outlet member 3 of the sampling module 7 to the filtering region 81 of the ion filtering module 8, up to the at least one detector 91 of the ion detecting module 9.

According to an implementation option, each of the processing chips 11, 12, 13 comprises a vacuum-proof covering member 54. Optionally, such a covering member 54 is also configured to physically separate the electronic part from the remaining functional part, but allowing an operational connection.

Figure 12:
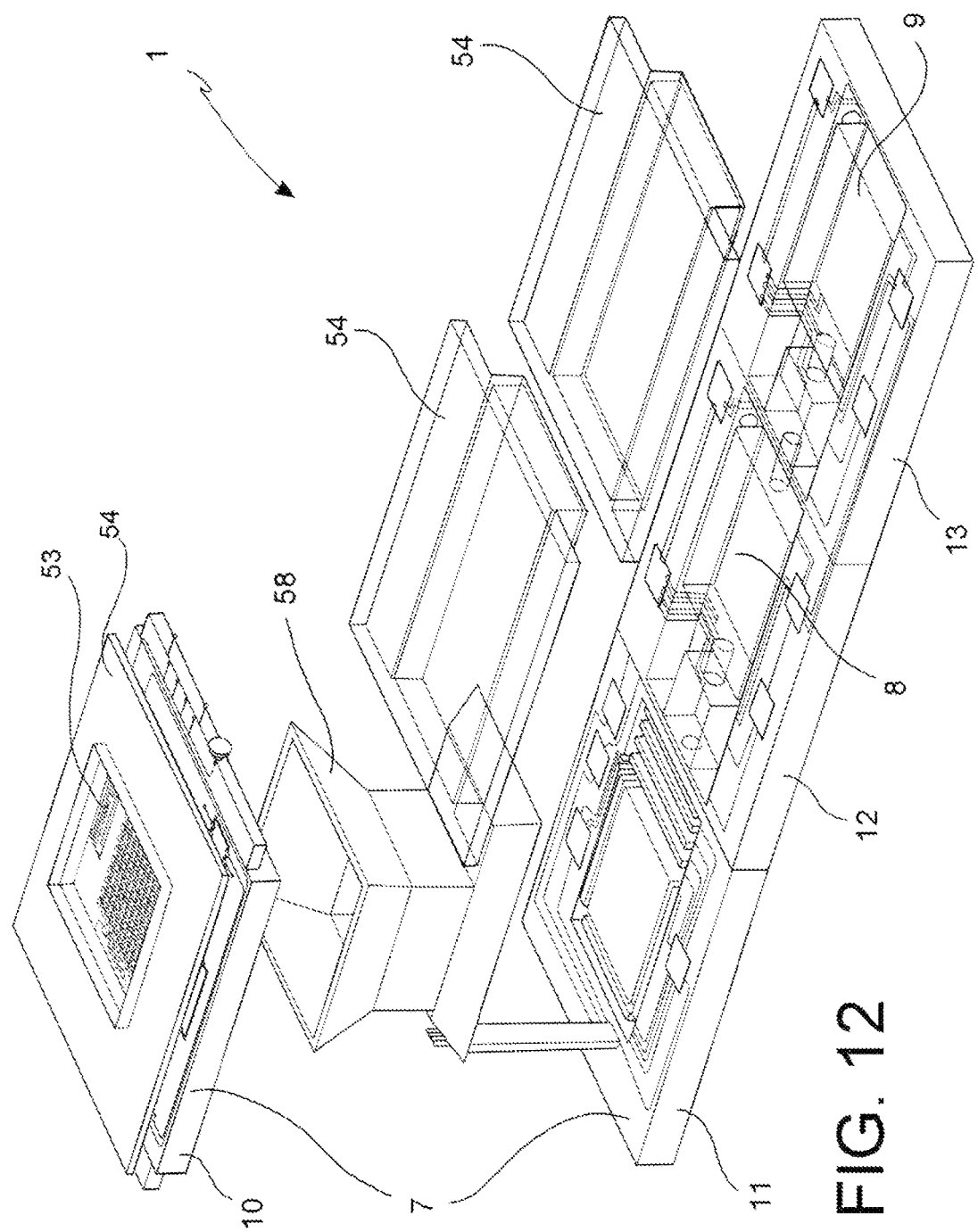
FIGS. 12 and 13 illustrate an exploded and perspective view, respectively, of a further embodiment of the device.
Figure 13:
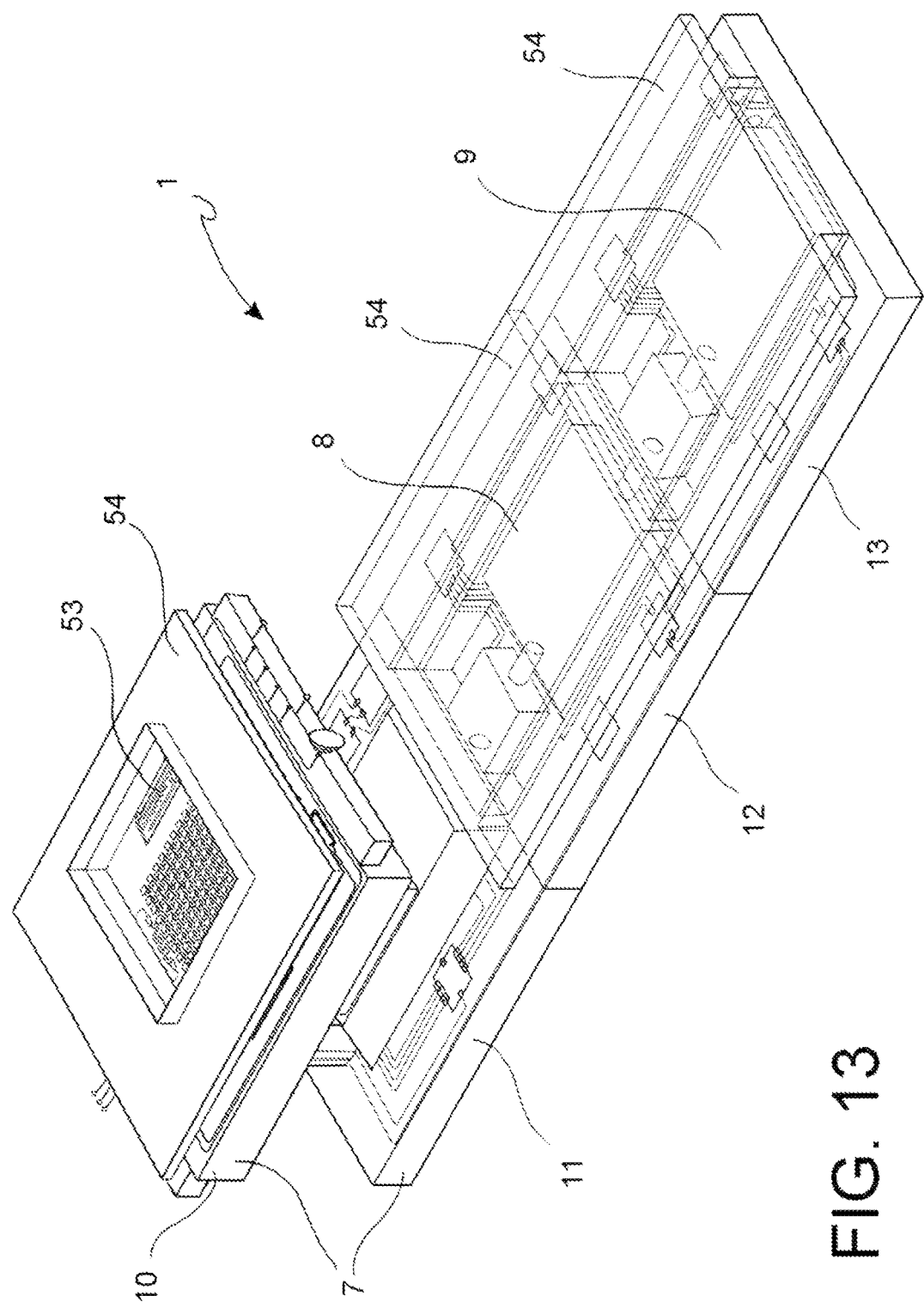

According to an embodiment, illustrated in FIGS. 12 and 13, the device 1 further is comprises a miniaturized connector member 58, integrated in the device 1, and configured to physically separate the interface and control chip 10 from the at least one processing chip 11, while, at the same time, allowing an operational connection between them.

Below, methods comprised in the invention will be described.

The invention comprises a method for automatically analyzing a gaseous composition in an environment A at an environment pressure Pa, by a portable analysis device 1.

The method comprises the steps of producing and maintaining ionization pressure conditions Pi inside the portable analysis device 1; then, adjusting an input gas flow Fi of gas particles from the environment A into a sampling module 7 of the device 1, and, in addition, adjusting an output gas flow Fo from the sampling module 7, in such a way that the input gas flow Fi is a flow at a molecular or predominantly molecular regime, at the environment pressure Pa, and the output gas flow Fo is a flow at a molecular or predominantly molecular regime, at the ionization pressure Pi, so that the gaseous composition in the sampling module 7 is representative of the gaseous composition to be analyzed.

The method then comprises the steps of ionizing the gaseous particles in the sampling module 7 so as to obtain an ion composition representative of the gaseous composition to be analyzed, and to extract from the sampling module 7 the ions generated, to generate an ion flow I having an ion composition representative of the gaseous composition to be analyzed.

The method also comprises the steps of controllably selecting, in a filtering module 8 of the portable analysis device 1, in communication with the sampling module 7, at least one type of ion that is present in said ion flow I, to generate a corresponding at least one homogeneous ion beam I', having an intensity representative of the concentration of the corresponding gas particle in the gaseous composition to be analyzed; then, extracting the above-mentioned at least one homogeneous ion beam I' from the ion filtering module 8, and measuring the intensity of the at least one ion beam I' by an ion detecting module 9 of the portable analysis device 1, to generate a corresponding electric signal S representative of the concentration of the corresponding gaseous particle in the gas composition to be analyzed.

According to a particular application example, the method further comprises, before performing the above-mentioned steps, the step of placing in the gaseous environment a device for the analysis of a gas composition 1 according to any of the embodiments previously described.

According to an example embodiment, the above-mentioned step of selecting further comprises the step of sequentially selecting a plurality of different types of ions present in the ion flow I, to obtain a respective sequence of ion beams I', so as to sequentially measure the concentrations of the gaseous particles of the composition to be analyzed.

According to another example embodiment, the above-mentioned step of selecting also provides spatially distinguishing a plurality of different types of ions present in the ion flow I; the above-mentioned step of extracting provides extracting the plurality of corresponding homogeneous ion beams I' from the filtering region; the above-mentioned step of measuring provides measuring in parallel, by respective detectors 91 comprised in the ion detecting module 9, the intensity of the homogeneous ion beams I', to generate respective electric signals S representative of the concentrations of the respective gaseous particles in the gaseous composition to be analyzed.

The invention also comprises a method of analysis of an industrial process carried out inside a processing environment at vacuum pressure, and emitting discharge gas externally to said processing environment.

This method comprises the steps of installing, in correspondence to the discharge opening of the discharge gases, a device 1 according to any of the embodiments previously described; then, analyzing the discharge gases, at a pressure that is different from the vacuum pressure, by means of the method according to any of the embodiments described above.

As can be seen, the object of this invention is achieved by the device described previously, by virtue of the characteristics illustrated.

From the above description, it is evident that the device of this invention is able to analyze a gas composition with great accuracy and, at the same time, the device can be built so as to be compact and portable, and even as an integrated and self-sufficient device.

In fact, due to the structure of the device, and to the related control functionality of the incoming gaseous flow, it is possible to operate starting from vacuum pressures, and adding, in a controlled way, gaseous micro-flows by injecting them into the device from the environment to be analyzed (which, generally, is not at vacuum pressure). So, contrary to the prior art, there is no need to proceed to pumping gaseous macro-flows towards the outside, in order to obtain the vacuum pressures necessary for ionization. Consequently, the ionization environment and the pumping means, as well as the other components of the device, can be easily miniaturized. At last, this allows implementing the device in a much more compact and less expensive manner compared to the known solutions cited, and thus obtaining a device that is portable and suitable to be easily installed anywhere.

Moreover, thanks to the fact that, as described above, the gaseous flows entering and exiting from the ionization environment are kept at a molecular or predominantly molecular regime, the device allows reproducing the gas composition to be analyzed, with great fidelity, in the ionization environment. This feature allows to considerably improve the accuracy and sensitivity of the analysis of gas composition.

In addition, by appropriately controlling the gaseous flows entering and exiting the ionization environment in the device, as described above, it is possible to enrich the density of gas particles in the ionization environment, while remaining at vacuum pressures compatible with ionization. This allows an improvement in the signal-to-noise ratio of the output signal, and therefore a further improvement of the sensitivity and accuracy of the device.

Finally, the diagnostic and self-adjustment procedures, mentioned above, allow the device to have a degree of self-sufficiency such as to make it versatile, reliable and suitable for a wide variety of uses.

Similar advantages can be identified in the methods for gas composition analysis previously described.

To the embodiments of the device for analyzing a gaseous composition, described above, and the related methods, a technician in the field, to satisfy contingent requirements, may make modifications, adaptations and replacements of members with others functionally equivalent, even jointly with the prior art, even creating hybrid embodiments, without departing from the scope of the following claims. Each of the characteristics described as belonging to a possible embodiment can be achieved independently from the other embodiments described. Also note that the term "comprising" does not exclude other elements or steps and the "a" or "one" does not exclude a plurality. Moreover, the figures are not necessarily to scale; on the contrary, importance is generally given to the illustration of the principles of this invention.

The invention claimed is:

1. An electronic device for analyzing a gaseous composition, which is present in an environment (A) at an environment pressure (Pa), the device being portable and suitable to be placed in said environment (A), and comprising:
   a gas sampling module, configured to adjust an input gas flow (Fi) of gas particles from said environment (A) and an output gas flow (Fo), so as to reproduce inside the sampling module a gaseous composition representative of said gaseous composition to be analyzed, and to ionize said gas particles and to emit the produced ions, so as to generate an ion flow (I) having an ion composition representative of the gaseous composition to be analyzed;
   an ion filtering module, operatively connected to the sampling module to receive the ion flow (I), and configured to controllably select at least one type of ions present in the ion flow (I) and to generate a corresponding at least one homogeneous ion beam (I'), having an intensity representative of the concentration of the corresponding gas particle in the gaseous composition to be analyzed;
   an ion detecting module, operatively connected to the ion filtering module to receive said at least one ion beam (I'), and configured to measure the intensity of the at least one ion beam (I') and to generate a corresponding electric signal (S) representative of the concentration of the corresponding gas particle in the gaseous composition to be analyzed;
   pumping means, configured to pump gas from the device, so as to control an ionization pressure (Pi) that is present inside the sampling module;
   wherein said input gas flow (Fi) comprises a plurality of micro-flows at a molecular or predominantly molecular regime, at the environment pressure (Pa), and said output gas flow (Fo) is a flow at a molecular or predominantly molecular regime, at the ionization pressure (Pi).

2. The device according to claim 1, wherein said device is an integrated device.

3. The device according to claim 1, wherein said environment pressure (Pa) is an atmospheric pressure or above, and said ionization pressure (Pi) is a vacuum pressure, ranging between $10^{-2}$ mbar and $10^{-3}$ mbar.

4. The device according to claim 1, wherein the sampling module comprises:
   an ionization chamber, suitable to be kept at the ionization pressure (Pi), and configured to contain and ionize said gas particles;
   an inlet member, configured to inhibit or allow and/or adjust an inlet in the ionization chamber of the input gas flow (Fi), and comprising a gaseous flow adjusting interface, having a plurality of nano-holes, of sub-micrometer dimensions, suitable to be opened or closed, in a controlled manner, to allow or inhibit said plurality of micro-flows at a molecular or predominantly molecular regime;
   an ion outlet member, operatively connected to the ion filtering module, configured to inhibit or allow and/or adjust said output gaseous flow (Fo), at a molecular or predominantly molecular regime, and the ion flow (I) of the generated ions.

5. The device according to claim 4, wherein said ion outlet member comprises an orifice, suitable to be opened or closed, in a controlled manner, so as to control an output conductance for the output gaseous flow (Fo),
   and wherein the sampling module further comprises:
   first actuating means, comprising a plurality of miniaturized nano-hole opening/closing members, each miniaturized opening/closing member being suitable to open or close a corresponding nano-hole, so as to maximize or minimize, respectively, the nano-hole conductance;
   second actuating means, comprising a shutter, configured to completely close, or to keep completely open, or partially occlude in a controlled manner the orifice of the ion outlet member;
   sampling module control means, configured to control the first and second actuating means.

6. The device (1) according to claim 4, wherein the ionization chamber comprises:
   at least one ionization source;
   an ionization region, containing gas particles that have entered through the gaseous flow adjusting interface, the ionization region being arranged so as to ionize the gas particles, and generate corresponding ions;

first ion extracting means, configured to determine a preferred trajectory for the generated ions, passing through at least one first ion extraction window, through which the ions exit the ionization region, and to subsequently guide the ions toward the ion outlet member;

ionization chamber control means.

7. The device according to claim 4, comprising:

an interface and a control chip, in which at least the gaseous flow adjusting interface and a first actuating means of the sampling module and electronic processing means are implemented;

at least one processing chip, in which the ionization chamber, the ion outlet member, and a second actuating means, of the sampling module, and, furthermore, the ion filtering module, the ion detecting module and the pumping means are implemented;

wherein the gaseous flow adjusting interface and the control chip overlaps the at least one processing chip, so that the corresponding portions of the sampling module match, and, furthermore, the interface and control chip is connected to the at least one processing chip so as to ensure a vacuum seal and to form a single integrated device;

wherein said at least one processing chip includes three processing chips, in which are implemented, respectively:

the ionization chamber, the ion outlet member, and the second actuating means, of the sampling module, the ion filtering module, the ion detecting module and the pumping means, said three processing chips being mutually connected in a vacuum sealed manner, so as to allow a passage of ions from the ion outlet member, of the sampling module, to a filtering region, of the ion filtering module, up to at least one detector of the ion detecting module.

8. The device (1) according to claim 1, wherein the ion filtering module comprises:

a filtering region, through which the ion beam (I) passes in order to be filtered, the filtering region comprising a second ion extraction window, through which said at least one homogeneous ion beam (I') exits the filtering region and the ion filtering module;

at least one electric and/or magnetic field generator, configured to generate in the filtering region an electric and/or magnetic field and/or potential, with an amplitude and/or frequency and/or spatial pattern that is variable in a controlled manner;

filtering module control means, configured to control said electric and/or magnetic field and/or potential in amplitude and/or frequency and/or spatial pattern, so as to control a trajectory or a filtering region passing-through speed, for the ions of the ion flow (I), as a function of the respective mass thereof.

9. The device according to claim 8, wherein the ion flow (I) comprises a plurality of ions of different type, having corresponding different masses, and wherein the filtering module control means are configured to select a type of ion:

either imposing a passing-through trajectory passing through the second extraction window, for particles having the same mass as that of the selected ion type, and passing-through trajectories which do not pass through the second extraction window, for particles having a different mass than that of the selected ion type;

or imposing a passing-through speed, for particles having the same mass as that of the selected ion type, such that said particles arrive at the second extraction window while it is open, and instead a different passing-through speed, for particles having a different mass than that of the selected ion type, such that said particles arrive at the second extraction window while it is closed, and wherein the device also comprises a further filtering member configured to form a chemical reaction cell, so as to distinguish ions of different chemical substances having an equivalent or similar mass.

10. The device (1) according to claim 8, wherein the filtering module control means comprises a plurality of second extraction windows, and the filtering module control means are configured to send in parallel different homogeneous ion beams (I'), corresponding to respective different types of ions, toward a respective one of the second extraction windows, and wherein the ion detecting module comprises a respective plurality of detectors and ion detecting module, the ion detecting module control means being configured to guide each of said homogeneous ion beams (I'), coming in parallel from the ion filtering module, toward a respective detector, so as to generate in parallel a plurality of electric signals (S), each being representative of a respective gas particle of the gaseous composition to be analyzed.

11. The device according to claim 1, wherein the ion detecting module comprises:

one or more detectors, each being configured to generate an electric signal (S) proportional to the intensity of the ion beam (I') incident therein;

detecting module control means.

12. The device according to claim 1, wherein the pumping means comprise a first pumping member installed in the filtering module, and/or a second pumping member installed in the sampling module, and/or a third pumping member installed in the ion detecting module, and wherein said pumping members are configured to determine the ionization pressure (Pi), a filtering pressure (Pf) inside the filtering module lower than the ionization pressure (Pi) and typically ranging between $10^{-5}$ and $10^{-7}$ mbar, and a detecting pressure (Pr) inside the detecting module that is lower than the filtering pressure (Pf) and ranging between $10^{-6}$ and $10^{-8}$ mbar.

13. A method for automatically analyzing a gaseous composition in an environment (A) at an environment pressure (Pa), by a portable analysis device, the method comprising the steps of:

producing and keeping ionization pressure (Pi) conditions inside a sampling module of the device;

adjusting an input gas flow (Fi) of gas particles from said environment (A) in the sampling module of the device, and adjusting an output gas flow (Fo) from the sampling module, in such a way that the input gas flow (Fi) is a flow at a molecular or predominantly molecular regime, at the environment pressure (Pa), and the output gas flow (Fo) is a flow at a molecular or predominantly molecular regime, at the ionization pressure (Pi), so that the gaseous composition in the sampling module is representative of the gaseous composition to be analyzed;

ionizing the gas particles inside the sampling module, so as to obtain an ion composition representative of said gaseous composition to be analyzed;

extracting the generated ions from the sampling module, to generate an ion flow (I) having an ion composition representative of said gaseous composition to be analyzed;

controllably selecting, in a filtering module of the portable analysis device, in communication with the sampling module, at least one type of ion that is present in said ion flow (I), to generate a corresponding at least one homogeneous ion beam (I'), having an intensity representative of the concentration of the corresponding gas particle in the gaseous composition to be analyzed;

extracting said at least one homogeneous ion beam (I') from the filtering module;

measuring the intensity of said at least one ion beam (I'), by an ion detecting module of the portable analysis device, to generate a corresponding electric signal (S) representative of the concentration of the corresponding gas particle in the gaseous composition to be analyzed.

14. The method according to claim 13, wherein:

the step of selecting comprises spatially or temporally distinguishing a plurality of different types of ions which are present in the ion flow (I);

the step of extracting comprises extracting the plurality of corresponding homogeneous ion beams (I') from a filtering region;

the step of measuring comprises measuring in parallel, by corresponding detectors comprised in the ion detecting module, the intensity of said homogeneous ion beams (I'), to generate respective electric signals (S) representative of the concentrations of the respective gas particles in the gaseous composition to be analyzed.

15. A method of analysis of an industrial process carried out inside a processing environment at vacuum pressure, the industrial process emitting discharge gas externally to said processing environment, the method comprising the steps of:

installing, at the discharge opening of the discharge gases, the portable analysis device according to claim 13;

analyzing the composition of the discharge gases, at a pressure that is different from the vacuum pressure, by carrying out a method for automatically analyzing a gaseous composition according to claim 13.

* * * * *